United States Patent [19]
Yeo

[11] Patent Number: 5,312,834
[45] Date of Patent: May 17, 1994

[54] PHARMACEUTICAL COMPOSITION FOR TREATING ACNE

[75] Inventor: Young K. Yeo, Taegu, Rep. of Korea

[73] Assignee: Woobang Land Co., Ltd., Taegu, Rep. of Korea

[21] Appl. No.: 866,991

[22] Filed: Apr. 10, 1992

[30] Foreign Application Priority Data

Apr. 10, 1991 [KR]  Rep. of Korea .................. 91-5731

[51] Int. Cl.$^5$ ............................................. A61K 31/20
[52] U.S. Cl. .................................... 514/560; 514/859
[58] Field of Search ................................ 514/560, 859

[56] References Cited

PUBLICATIONS

Chemical Abstracts 113:55072w (Ando et al.), 1989.
Biochimica et Biophysica Acta, 1006 (1989) 9–14, Elsevier.
Biochimica et Biophysica Acta 1001 (1989) 25–30, Elsevier.
Journal of Pathology, vol. 156; 101–110 (1988) K. I. Williams and G. A. Higgs.

Primary Examiner—Marianne M. Cintins
Attorney, Agent, or Firm—Birch, Stewart, Kolasch & Birch

[57] ABSTRACT

A pharmaceutical composition for treating acne includes eicosapentaenoic acid and α-linolenic acid, in a weight ratio of 1:0.1 to 20.0 of eicosapentaenoic acid to α-linolenic acid, respectively, and, optionally, vitamin E as an antioxidant. Eicosapentaenoic acid and α-linolenic acid, which are effective components of the composition of the present invention, may be extracted from natural substances such as fish oil and perilla oil, respectively.

23 Claims, No Drawings

PHARMACEUTICAL COMPOSITION FOR TREATING ACNE

BACKGROUND OF THE INVENTION

1. Field of the Invention

The present invention relates to a pharmaceutical composition for treating acne. More particularly, the present invention relates to a therapeutic composition for treating acne, which includes eicosapentaenoic acid and α-linolenic acid.

2. Description of the Prior Art

Pharmaceutical compositions for treating acne generally include ointments containing synthetic chemicals, especially hormones, as an active ingredient, and are well known in the art. However, such prior art compositions suffer from a number of disadvantages such as, for example, (a) the application thereof results in greatly different skin reactions for every patient and, therefore, each composition must be carefully selected, (b) the compositions may cause severe allergic reactions and thus complicate the skin problems rather than treat the acne, and (c) when the treatment is discontinued, acne readily reoccurs.

The specific cause of acne is not yet clearly identified. It is only well known that the cause of inflammatory skin conditions such as acne, etc., is leukotrienes $B_4$, $C_4$, $D_4$, $E_4$ and the like, produced by the degradation of arachidonic acid, which is a constituent of phospholipids present in the skin endothelium. This is caused by the action of several enzymes such as, for example, 5-lipoxygenase, glutathione peroxidase, hydrolase, glutamyl transferase, glutamyl transpeptidase, dipeptidase, etc. In addition, it has been disclosed that the other cyclooxygenase enzymatic degradation products, i.e., prostaglandin $E_2$ and thromboxane $B_2$, may cause skin inflammation.

Furthermore, patients may produce skin-sensitive degradation products because of their health condition. Such degradation products may also act as one of the causes of skin acne or of the worsening of the acne condition. Among the above-mentioned causes, it is commonly and clearly recognized that arachidonic acid, as the primary degradation product of skin phospholipids, is decomposed to produce several degradation products which act as causes of acne.

Phospholipids present in the cell membrane of the facial skin tissue contain a great quantity of arachidonic acid. Arachidonic acid is converted into free arachidonic acid by the action of phospholipase $A_2$ and then is metabolized by cyclooxygenase to produce 2-series prostaglandins, and then by lipoxygenase to produce 4-series leukotrienes. Among these metabolites, particularly prostaglandin $E_2$, thromboxane $B_2$, leukotrienes $B_4$, $C_4$, $D_4$, $E_4$ and the analogs thereof, may act as the cause of numerous inflammatory conditions in human body.

For example, Simmons et al (Biochemistry and Pharmacology, 1983) and Haworth et al (Inflammatory Mediators, 1985) have demonstrated that leukotriene $B_4$ is present in large quantity in acute inflammatory tissue. In addition, Robinson et al (Prostaglandins, 1975) have reported that prostaglandin $E_2$ is the cause of inflammatory conditions. Accordingly, extensive studies have been conducted to find a method for preventing the binding of arachidonic acid to cell membrane phospholipids and inhibiting the production of eicosanoids from arachidonic acid.

Thus, Yoe et al (Biochimica et Biophysica Acta, 1989a), who are also the inventors of the present invention, showed that a drastic reduction in the amount of arachidonic acid in cell membranes could be achieved by replacing arachidonic acid (an n-6 fatty acid) with eicosapentaenoic acid (EPA), which is an n-3 fatty acid. Also, Yeo et al have demonstrated the substitution effect of eicosapentaenoic acid for arachidonic acid by confirming that the biosynthesis of arachidonic acid significantly decreases while the biosynthesis of eicosapentaenoic acid and docosahexaenoic acid greatly increases from the examination of the synthesis of various fatty acids in experimental animals (Sprague-Dawley rats) to which eicosapentaenoic acid is administered and then ($^3$H) glycerol is injected.

SUMMARY OF THE INVENTION

Accordingly, it is an object of the present invention to provide a pharmaceutical composition for treating acne, which eliminates the above problems encountered in prior art acne therapeutic compositions.

Another object of the present invention is to provide an acne therapeutic composition which includes eicosapentaenoic acid and α-linolenic acid.

A further object of the present invention is to provide a pharmaceutical composition which can remove the cause of acne by blocking the degradation of arachidonic acid having the following formula.

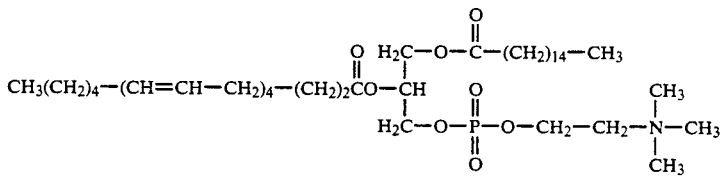

1-Palmityl-2-arachidonyl-sn-glycero-3-phophocholine, is a compound of the structure of the above formula, is the most predominant phospholipid of skin phospholipids.

Yet another object of the present invention is to provide a therapeutic agent for treating acne using natural substances, which are not synthetic chemical substances, but which contains a natural substance or an effective component obtained by extraction and separation from natural sources.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

Briefly described, the present invention relates to a pharmaceutical composition for treating acne which includes eicosapentaenoic acid and α-linolenic acid in a weight ratio of 1:0.1 to 20.0, and vitamin E as an antioxidant. Eicosapentaenoic acid and α-linolenic acid, which are effective components of the composition of the present invention, are extracted from natural sources such as fish oil and perilla oil, respectively.

DESCRIPTION OF THE PREFERRED EMBODIMENTS

Referring now in detail to the present invention, there is provided an acne therapeutic composition for medical use, which contains eicosapentaenoic acid and α-linolenic acid for completely removing the cause of acne which has been difficult to treat and prevent heretofore.

The present inventors have studied the cause of such undesirable skin reactions from a wide variety of angles. As a result, they have discovered that a reason why the treatment of acne is difficult is that the skin itself is especially susceptible to allergic conditions. Such allergic reactions greatly vary with every person. The synthetic chemicals contained in most agents for the treatment of acne may themselves also be the cause of such allergic reactions. Moreover, minor amounts of impurities, such as for example solvents or other chemical reagents, which unavoidably accompany the synthetic active chemical because of manufacturing processes cause the skin allergic skin conditions to worsen.

In the present invention, since fish oil is rich in eicosapentaenoic acid, it is expected that the administration of fish oil will be significantly effective for the treatment of acne. When fish oil is administered to the extent that acne can be treated, the eicosapentaenoic acid; of the fish oil is decomposed in the body to produce toxic aldehydes such as malondialdehyde, which may cause side effects.

Therefore, in order to minimize the aldehyde decomposition product, the dosage of fish oil should be reduced. However, the reduction of the dosage of fish oil also results in a decrease in the effect of treating acne. Thus, the present invention provides a therapeutic composition in which a portion of the fish oil content is replaced with perilla oil or linseed oil having a high α-linolenic acid content. The oil has no side effects, but exhibits the same effect as eicosapentaenoic acid of fish oil, and is employed to be very effective for the treatment of acne as compared to the administration of fish oil only, without the danger of aldehyde toxicity. Thus, the present invention encompasses a pharmaceutical composition for treating acne, which comprises fish oil containing eicosapentaenoic acid, perilla oil containing α-linolenic acid, and a pharmaceutically acceptable auxiliary. Vitamin E can be added as an antioxidant.

The present invention also encompasses a pharmaceutical composition for treating acne, which comprises fish oil containing eicosapentaenoic acid, linseed oil containing α-linolenic acid, and a pharmaceutically acceptable auxiliary. Vitamin E can be added as an antioxidant.

The mechanism of α-linolenic acid in the treatment of acne has not yet been clearly established. It is recognized that α-linolenic acid itself blocks the conversion of linoleic acid into arachidonic acid and, further, some of the α-linolenic acid is converted into eicosapentaenoic acid which exhibits a therapeutic effect on acne.

The fish oil which can be used in the present invention is not limited by the type of fish. A fish oil having a high eicosapentaenoic acid content is usually uneconomical due to its high price, and fish oil having too low a content of eicosapentaenoic acid is less effective. Accordingly, the selection of fish oil and the mixing ratio between the fish oil and the perilla oil or linseed oil containing α-linolenic acid may exert a significant effect upon the quality of the resulting composition, as well as the economical and commercial consequences. Although commercially available fish oil contains generally about 5 to 30% of eicosapentaenoic acid, the content of eicosapentaenoic acid may be increased by purification utilizing the difference in melting points. Linseed oil and perilla oil contain 40 to 70% and 30-70% α-linolenic acid, respectively.

The present invention provides a natural pharmaceutical composition which contains fish oil and perilla oil in various mixing ratios. It is noted that although the content or mixing ratio of fish oil and perilla oil is not specifically limited, in general, any fish oil containing about 5 to 40% eicosapentaenoic acid can be used, and perilla oils with an α-linolenic acid content of about 30 to 70% can yield satisfactory results. In addition, the mixing ratio between the fish oil and the perilla oil or linseed oil may vary depending on the content of the effective component contained in respective oil. On the basis of the effective components the composition, a mixing ratio of 0.1 to 20 g of α-linolenic acid to 1 g of eicosapentaenoic acid can exhibit an acceptable therapeutic effect on acne, with a mixing ratio of 3.0 to 10.0 g of α-linolenic acid to 1 g of eicosapentaenoic acid being preferable.

If the content of eicosapentaenoic acid is too high as compared with that of α-linolenic acid, adverse effect due to the formation of high amounts of toxic aldehydes may be expected. On the contrary, if the content of eicosapentaenoic acid is too low, the therapeutic effect on acne may be poor. When fish oil is used as the source of eicosapentaenoic acid and perilla oil is used as the source of α-linolenic acid, the therapeutic effect on acne can be attained at a mixing ratio of fish oil to perilla oil of about 1:0.1-10.0 by volume. In addition, when linseed oil is used as the source of α-linolenic acid, since the content of α-linolenic acid in linseed oil is about 40 to 70%, effective treatment of acne is possible at a mixing ratio of fish oil to linseed oil of 1:0.2-12.0 by volume.

The composition of the present invention can also contain pharmaceutically acceptable preservatives, antioxidants, etc. The composition of the present invention may be administered in the form of syrups or may be concentrated and filled in soft capsules. As the antioxidant to be used in the present invention, vitamin E is suitable. Such an antioxidant plays the role of inhibiting the formation of aldehydes. Although the dosage to be administered may be varied depending on the condition of the acne, it is preferable to administer about 2 to 5 g of eicosapentaenoic acid and 5 to 30 g of α-linolenic acid per day which may be divided into two to five treatments.

Accordingly, when a composition containing commercially available fish oil with 18% eicosapentaenoic acid and perilla oil with 55-60% α-linolenic acid in a ratio of 1:2 by weight is used, a satisfactory therapeutic effect can be obtained by administering one spoon (15 ml) of the composition every eight hours, three times a day.

The effect of the composition of the present invention is shown by the following clinical experiment.

A. Preparation of the Composition

A liquid therapeutic composition for acne is prepared by mixing fish oil containing 18% eicosapentaenoic acid with perilla oil containing 57.6% α-linolenic acid in a the ratio of 1:2 by weight and adding a suitable amount of vitamin E as antioxidant. For this purpose, the Max-EPA oil filled in soft capsules, which is commercially available in Europe and America, is used as the fish oil. As the perilla oil, perilla seeds of *Perilla frutescens* var. *japonica* are pressed by means of a 2.5 ton compressor to obtain oil which is then filled in a container, and the container is sealed and then stored at 5° C. for 24 hours and then the supernatant oil is used.

B. Experimental Method

The liquid composition as prepared above was administered to 6 school boy volunteers and 6 school girl volunteers, who have severe acne, in an amount of 15 ml every 8 hours, three times a day. The therapeutic result was examined every week.

C. Experimental Result

The results of the acne treatment in the volunteer students was analyzed as follows. The acne condition at the beginning of experiment is indicated as 10, and the entire disappearance of acne is indicated as 0. The acne condition was recorded every week after administration of the composition.

Experimental Result for acne treatment effect of the composition of the present invention

| volunteer | after 0 week | after 1 week | after 2 week | after 3 week | after 4 week | after 5 week | after 6 week | after 7 week | after 8 week |
|---|---|---|---|---|---|---|---|---|---|
| Boy 1 | 10 | 9 | 5 | 3 | 1 | 0 | | | |
| Boy 2 | 10 | 8 | 5 | 3 | 1 | 1 | 0 | | |
| Boy 3 | 10 | 9 | 6 | 4 | 2 | 1 | 0 | | |
| Boy 4 | 10 | 10 | 7 | 4 | 2 | 1 | 0 | | |
| Boy 5 | 10 | 9 | 6 | 3 | 1 | 0 | | | |
| Boy 6 | 10 | 9 | 6 | 3 | 1 | 0 | | | |
| Girl 1 | 10 | 8 | 6 | 3 | 2 | 1 | 0 | | |
| Girl 2 | 10 | 10 | 8 | 6 | 5 | 3 | 2 | 1 | 0 |
| Girl 3 | 10 | 9 | 5 | 3 | 2 | 1 | 0 | | |
| Girl 4 | 10 | 9 | 7 | 5 | 3 | 2 | 1 | 0 | |
| Girl 5 | 10 | 10 | 8 | 7 | 6 | 4 | 2 | 1 | 0 |
| Girl 6 | 10 | 8 | 6 | 5 | 3 | 2 | 1 | 0 | |

As shown above, in all cases the acne was completely treated within 4 weeks to 8 weeks after administration of the acne therapeutic composition of the present invention, although there is some difference between the subject patients. In addition, the composition of the present invention further provides for good color and resilience of the skin. Therefore, it is evident that the composition of the present invention has an excellent effect in the treatment of acne and further, for skin beauty treatment.

Hereinafter, the preparation of examples of the composition of the present invention are illustrated. However, of course, it should be understood that the following examples are not intended to limit the scope of the present invention.

PREPARATION EXAMPLE 1

| | |
|---|---|
| Fish oil (containing 18% eicosapentaenoic acid) | 100 ml |
| Perilla oil (containing 57.6% α-linolenic acid) | 200 ml |
| Vitamin E | 0.15 g |
| Sweetener | q.s. |

100 ml of fish oil is mixed with 200 ml of perilla oil. To this mixture are added 0.15 g of vitamin E and sweetener to prepare the liquid therapeutic composition for acne which is then stored in a shaded sealed container.

PREPARATION EXAMPLE 2

| | |
|---|---|
| Fish oil (containing 25% eicosapentaenoic acid) | 100 ml |
| Perilla oil (containing 60% α-linolenic acid) | 200 ml |
| Vitamin E | 0.17 g |
| Sweetener | q.s. |

According to the same method as Preparation Example 1, fish oil, perilla oil, vitamin E as antioxidant, and sweetener are mixed together to prepare the therapeutic liquid composition for acne.

PREPARATION EXAMPLE 3

| | |
|---|---|
| Fish oil (containing 10% eicosapentaenoic acid) | 100 ml |
| Perilla oil (containing 50% α-linolenic acid) | 200 ml |
| Vitamin E | 0.12 g |
| Sweetener | q.s. |

According to the same method as Preparation Example 1, the above-identified components are mixed together to prepare the therapeutic liquid composition for acne.

PREPARATION EXAMPLE 4

| | |
|---|---|
| Fish oil (containing 15% eicosapentaenoic acid) | 100 ml |
| Linseed oil (containing 49% α-linolenic acid) | 200 ml |
| Vitamin E | 0.13 g |
| Sweetener | q.s. |

According to the same method as Preparation Example 1, the therapeutic liquid composition for acne, which is composed of the above identified components, is prepared.

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A pharmaceutical composition for treating acne, which consists essentially of effective amount of eicosapentaenoic acid, α-linolenic acid and a pharmaceutically acceptable auxiliary.

2. The pharmaceutical composition of claim 1, wherein a the ratio of said eicosapentaenoic acid to said α-linolenic acid is about 1:0.1 to 20.0 by weight.

3. The pharmaceutical composition of claim 2, wherein said ratio of eicosapentaenoic acid to α-linolenic acid is 1:3.0–10.0 by weight.

4. A pharmaceutical composition for treating acne, which consists essentially of and effective amount of eicosapentaenoic acid, alpha-linolenic acid, vitamin E as an antioxidant and a pharmaceutically acceptable auxiliary.

5. A pharmaceutical composition for treating acne, which comprises fish oil containing eicosapentaenoic acid, perilla oil containing α-linolenic acid, and a pharmaceutically acceptable auxiliary.

6. The pharmaceutical composition of claim 5, wherein the content of eicosapentaenoic acid in said fish oil is about 5 to 40% and the content of α-linolenic acid in said perilla oil is about 30 to 70%.

7. The pharmaceutical composition of claim 5, wherein the ratio of said fish oil to said perilla oil is 1:0.1–10.0 by volume.

8. The pharmaceutical composition of claim 5, wherein vitamin E is added to said pharmaceutical composition as an antioxidant.

9. A pharmaceutical composition for treating acne, which consists essentially of fish oil containing eicosapentaenoic acid, linseed oil containing α-linolenic acid, and a pharmaceutically acceptable auxiliary.

10. The pharmaceutical composition of claim 9, wherein content of eicosapentaenoic acid in said fish oil is about 5 to 40% and the content of α-linolenic acid in said linseed oil about is 40 to 70%.

11. The pharmaceutical composition of claim 9, wherein the ratio of said fish oil to said linseed oil is 1:0.2–12.0 by volume.

12. A pharmaceutical composition for treating acne, which consists essentially of fish oil containing eicosapentaenoic acid, alpha-linolenic acid, vitamin E as an antioxidant and a pharmaceutically acceptable auxiliary.

13. The pharmaceutical composition of claim 1, wherein said pharmaceutically acceptable auxiliary is a member selected from the group consisting of a preservative and an antioxidant.

14. The pharmaceutical composition of claim 1, wherein said composition is in the form of a syrup or a soft capsule.

15. A method of treating acne, comprising administering to a subject about 2 to 5 grams of eicosapentaenoic acid and 5 to 30 grams of α-linolenic acid per day.

16. The method of claim 15, wherein said eicosapentaenoic acid and said α-linolenic acid are administered in 2 to 5 treatments per day.

17. A pharmaceutical composition for treating acne, which comprises fish oil containing 18% eicosapentaenoic acid and perilla oil containing 55 to 60% α-linolenic acid in a ratio of 1:2 by weight.

18. A method of treating acne, comprising administering 15 milliliters of said composition of claim 17 every 8 hours, 3 times per day.

19. The pharmaceutical composition of claim 17, further comprising Vitamin E as an antioxidant.

20. A pharmaceutical composition for treating acne, which comprises 100 milliliters of fish oil containing 18% eicosapentaenoic acid, 200 millimeters of fish oil containing 18% eicosapentaenoic acid, 200 milliliters of perilla oil containing 57.6% α-linolenic acid, 0.15 grams of Vitamin E, and a sweetener.

21. A pharmaceutical composition for treating acne, which comprises 100 milliliters of fish oil containing 25% eicosapentaenoic acid, 200 milliliters of perilla oil containing 60% α-linolenic acid, 0.17 grams of Vitamin E, and a sweetener.

22. A pharmaceutical composition for treating acne, which comprises 100 milliliters of fish oil containing 10% eicosapentaenoic acid, 200 milliliters of perilla oil containing 50% α-linolenic acid, 0.12 grams of Vitamin E, and a sweetener.

23. A pharmaceutical composition for treating acne, which comprises 100 milliliters of fish oil containing 15% eicosapentaenoic acid, 200 milliliters of linseed oil containing 49% α-linolenic acid, 0.13 grams of Vitamin E, and a sweetener.

* * * * *